United States Patent [19]

Scott

[11] Patent Number: 5,522,251

[45] Date of Patent: Jun. 4, 1996

[54] METHODS AND APPARATUS FOR SIMULATING THE LONG-TERM EFFECTS OF NORMAL WEAR AND MAINTENANCE OF SURFACES

[75] Inventor: Graham A. H. Scott, LaGrange, Ga.

[73] Assignee: Interface, Inc., LaGrange, Ga.

[21] Appl. No.: 413,923

[22] Filed: Mar. 29, 1995

Related U.S. Application Data

[63] Continuation of Ser. No. 965,169, Oct. 23, 1992, abandoned.

[51] Int. Cl.$^6$ .................................................. G01N 3/56
[52] U.S. Cl. ........................... 73/7; 73/856.6; 434/365
[58] Field of Search ........................... 73/7, 9, 10, 865.6; 434/365, 366; 134/21, 57 R, 80, 85, 86, 88

[56] References Cited

U.S. PATENT DOCUMENTS

| | | | |
|---|---|---|---|
| 2,895,326 | 7/1959 | Fesperman et al. | 73/7 |
| 2,966,790 | 1/1961 | Walker | 73/7 |
| 3,688,556 | 9/1972 | Bigelow | 73/7 |
| 4,569,222 | 2/1986 | Arnold et al. | 73/9 |
| 5,281,535 | 1/1994 | Wei et al. | 73/9 |

FOREIGN PATENT DOCUMENTS 0270589  8/1989  Germany .................................. 73/7

OTHER PUBLICATIONS

Operating Instructions and other materials relating to a Roller Chair Testing Device 28167 of Feingerate Baumberg, six pages (1989).

"Instrumentation to Impose and Assess Carpet Wear," *Notes on Research* No. 425 (Jun. 1989).

"Appearance Retention of Nine Carpet Samples," *Research Services Report* No. 266 (Dec. 15, 1989).

Schiefer et al, "Carpet Wear Testing Machine", Jun. 1931, pp. 927–936.

Irwin, W. E., "Development of a method to measure wear on resilient flooring", Jan. 1976, pp. 15–20.

Gavan, F. M., "The Wear Testing of Carpets and Resilient Floorings", Jul. 1970, pp. 24–28.

Brochure of Simuwear Corporation Entitled "Evaluating . . . . Floor Covering Performance . . ." (six pages; circa 1994).

Press Releases of G. Wentworth Smith, Inc. entitled "Foot--Force Simulator-Test Technology Unveiled" and Foot Force Simulator Tests Carpet (Columbus, Wisconsin; Jul. 18, 1993; three pages).

Price List of G. Wentworth Smith, Inc. entitled "Wentworth Smith Foot Force Simulator Testing Services Price List" (Columbus, Wisconsin; Aug. 1, 1993; one page).

*Primary Examiner*—Hezron E. Williams
*Assistant Examiner*—Nashmiya Ashraf
*Attorney, Agent, or Firm*—Dean W. Russell; Kilpatrick & Cody

[57] ABSTRACT

A system for simulating effects of cleaning and maintenance on the appearance of a product such as carpet tile is disclosed. Short- and long-term effects of wear and soiling can be simulated as well, providing a relatively complete and rapid indicator of product appearance changes over time.

7 Claims, 15 Drawing Sheets

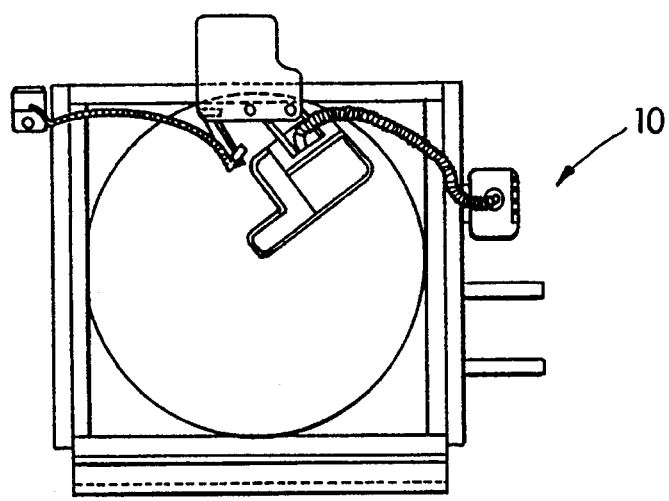
FIG.13B
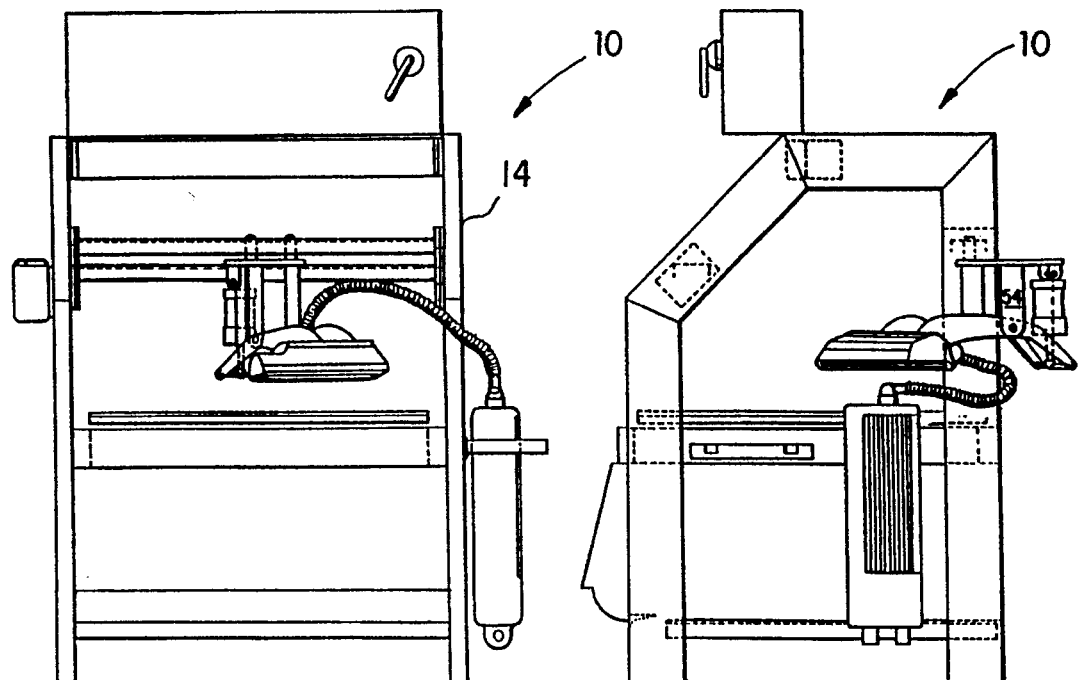
FIG.13A
FIG.13C

METHODS AND APPARATUS FOR SIMULATING THE LONG-TERM EFFECTS OF NORMAL WEAR AND MAINTENANCE OF SURFACES

This is a continuation of application Ser. No. 07/965,169 filed on Oct. 23, 1992, now abandoned.

This invention relates to systems for testing and evaluating appearance and other aspects of the surfaces of materials such as carpets or carpet tiles.

BACKGROUND OF THE INVENTION

Product appearance is an important consideration for many would-be purchasers of floor coverings including carpets or carpet tiles. Consequently, manufacturers frequently expend substantial time and effort in creating products with aesthetically-pleasing surfaces. Substantial effort is additionally consumed in seeking to develop surfaces that retain aspects of their appearance over time, counteracting the altering effects of, among other things, wear from normal usage, cleaning, and maintenance.

Determining whether carpet tiles retain their appearance over time is presently typically a lengthy or inexact task. Of course, among the simplest methods is to place product samples in a suitable environment for the length of the period at issue. Because the useful life of most carpet tiles is defined in years, however, a testing period equalling the tile's useful life is far too long to represent an efficient use of resources.

Alternatively, devices exist that simulate carpet surface wear by repeatedly contacting the surface with one or more castors. These "wear testing" devices (including the Roller Chair Testing Device 28167 of Feingerate Baumberg) do not account for appearance changes caused by cleaning or maintenance, for example, nor do they contemplate possible soiling of the surface itself over time. The devices additionally use discrete weights to force single-sized, fixed-position castors against the surface under test, limiting their capability in that regard. Other devices such as the TRI carpet walker described in "Instrumentation to Impose and Assess Carpet Wear," *Notes on Research No.* 425 (June 1989), which report is incorporated herein in its entirety by this reference, affix sneaker sole material to a cylinder in an effort to assess the appearance-change effects of walking on a carpet surface over time. Like "wear testing" devices, however, the TRI carpet walker too neglects the effects of cleaning and maintenance on the surface of the product.

SUMMARY OF THE INVENTION

By contrast, the present invention provides a system for simulating effects of cleaning and maintenance on the appearance of a product such as carpet tiles. Short- and long-term effects of wear and soiling can be simulated as well, permitting a more complete indicator of product appearance changes over time than was previously available. The innovative simulation additionally reduces to minutes the amount of time needed to conduct long-term analysis of appearance changes. Thus, multiple iterations using different cleaning and maintenance chemicals and devices, for example, can be made in an effort to develop a maintenance program optimizing appearance-retention results.

In one embodiment of the invention for use with carpet tiles, a microprocessor-controlled, electro-mechanical apparatus cycles sample tiles through various cleaning and maintenance actions. The sample carpet tiles are placed on a turntable and rotated and initially contacted with castors included on a counterrotating wheel. Unlike existing wear testing devices, the apparatus utilizes continuously variable quantities of air pressure to force the castors against the carpet tile surface. The apparatus additionally permits castors of differing diameters to be used in varying positions, allowing more flexibility in creating the simulated environment.

Following initial contact with the castors during a cycle, the sample tiles are subjected to sequenced cleaning and maintenance activities normally encountered during use. A carpet sweeper (dry vacuum), shampoo head, and extraction vacuum head subsequently contact the surface of the tiles, with the turntable repeatedly reversing rotation direction during carpet sweeping to simulate the motion frequently used during manual sweeping. Rotation speed of the turntable also may be varied during the simulation, and a hot-air dryer employed to accelerate drying of the samples. As currently estimated, such an embodiment accelerates aging of the samples so that 30–60 minutes under test is approximately equivalent (or at least on the order of) one year of normal use. A fifteen-year simulation, therefore, can be conducted during a single eight-hour day.

Embodiments of the present system also contemplate use of an automatic device for soiling the samples under test, typically prior to the cleaning and maintenance activities of a particular cycle. A pre-spray mechanism can also be included to loosen accumulated soil from the samples, as can devices designed to measure, for example, the moisture content of the samples as a function of time. By evaluating the color spectra and chemical composition of the fluid removed from the carpet tiles by the extraction vacuum, characteristics of the tiles including dye fastness and chemical integrity can be evaluated as well.

It is therefore an object of the present invention to provide a system accounting for effects of cleaning and maintenance on the appearance of carpet tiles or functionally-similar products.

It is another object of the present invention to provide a system for simulating other appearance-altering effects caused by, for example, soiling or wear.

It is an additional object of the present invention to provide a system useful in developing a product maintenance program designed to increase the product's appearance retention capabilities as a function of time.

It is a further object of the present invention to provide a system for testing the short- and long-term effects of particular maintenance procedures on a product, including any given carpet construction.

It is yet an additional object of the present invention to provide a system capable of duplicating a variety of maintenance procedures for carpeting and other products.

It is another object of the present invention to provide an electro-mechanical apparatus subjecting a product to desired sequences of actions automatically.

It is a further object of the present invention to provide an apparatus for moving a product automatically relative to various testing equipment such as a wear device and shampoo and vacuuming heads.

Other objects, features, and advantages of the present invention will become apparent with reference to the remainder of the written portion and the drawings of this application.

BRIEF DESCRIPTION OF THE DRAWINGS

FIGS. 1–14 are various views (some partially cut-away or schematicized) of an embodiment of the apparatus useful as part of the present invention.

FIG. 1 is a front elevational view of a portion of the apparatus illustrating, for example, a shampoo head as part of the present invention.

FIG. 2 is a front elevational view of a portion of the apparatus illustrating, for example, a vacuum head as part of the present invention.

FIG. 3 is a side elevational view of the portion of the apparatus of FIG. 2.

FIG. 4 is a front elevational view of a portion of the apparatus illustrating, for example, a carpet sweeper as part of the present invention.

FIG. 5 is a side elevational view of the portion of the apparatus of FIG. 4.

FIG. 6 is a front elevational view of a portion of the apparatus illustrating, for example, a wear-causing device of the present invention.

FIG. 7 is a side elevational view of the portion of the apparatus of FIG. 6.

FIG. 8 is a front elevational view of a portion of the apparatus illustrating, for example, a dryer as part of the present invention.

FIG. 9 is a side elevational view of the portion of the apparatus of FIG. 8.

FIG. 10 is a perspective view of the apparatus useful as part of the present invention.

FIG. 11 is top plan view of a portion of the apparatus useful as part of the present invention.

FIGS. 13A–C are views of a portion of the apparatus illustrating, for example, the carpet sweeper of FIGS. 4–5 together with a pre-spray mechanism.

DETAILED DESCRIPTION

A. Structure

Figure 1:
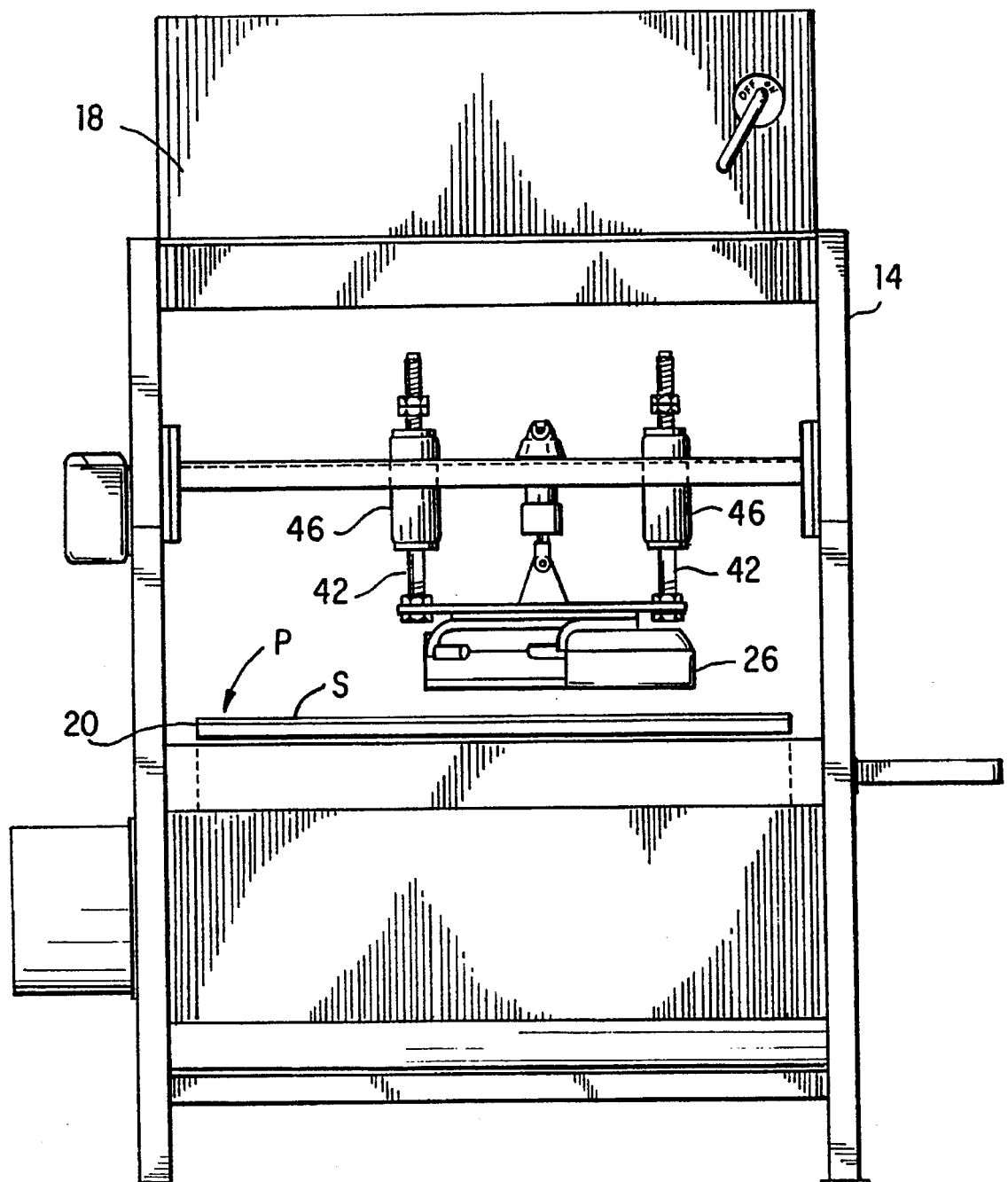
Figure 2:
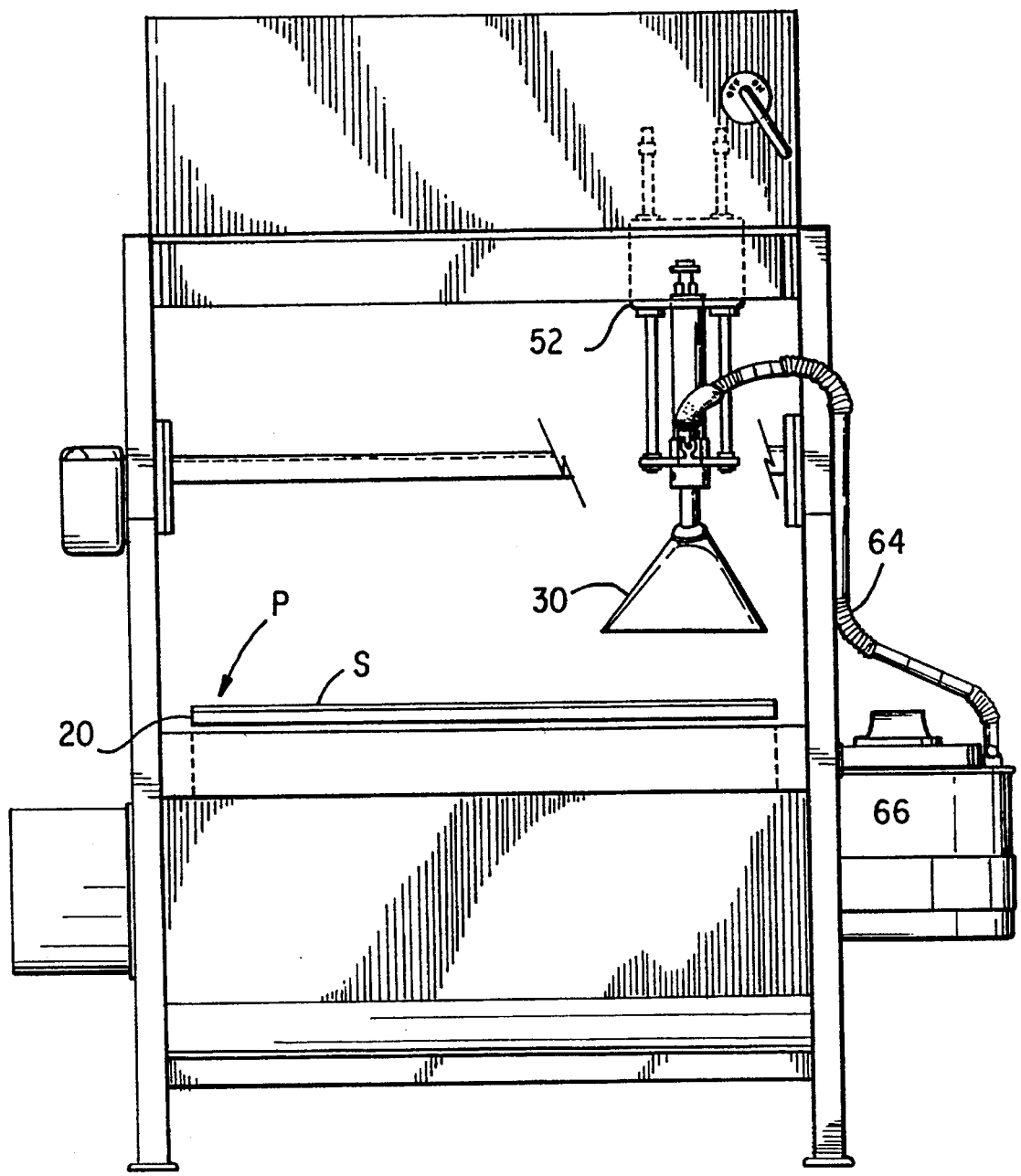
Figure 3:
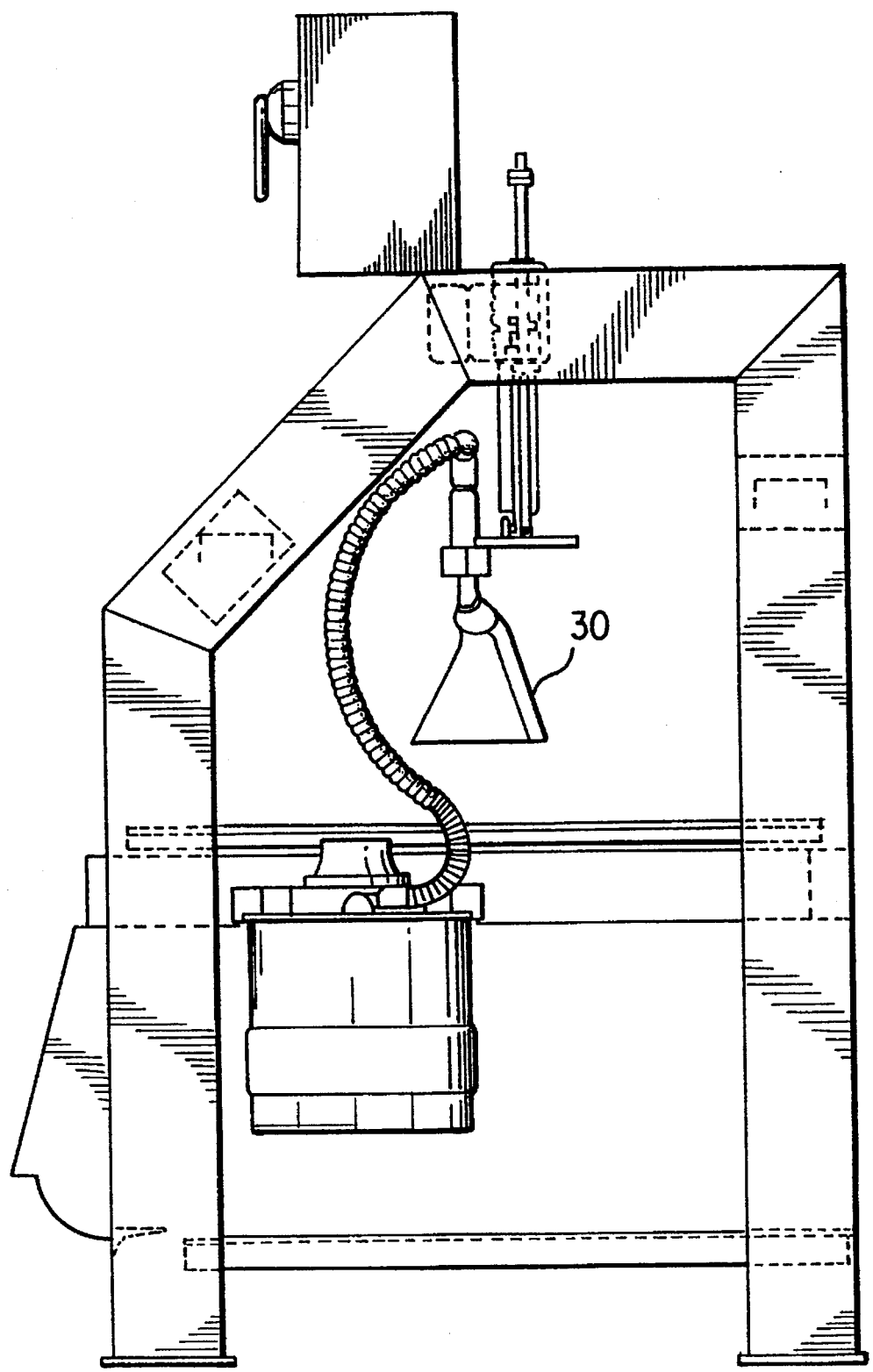
Figure 4:
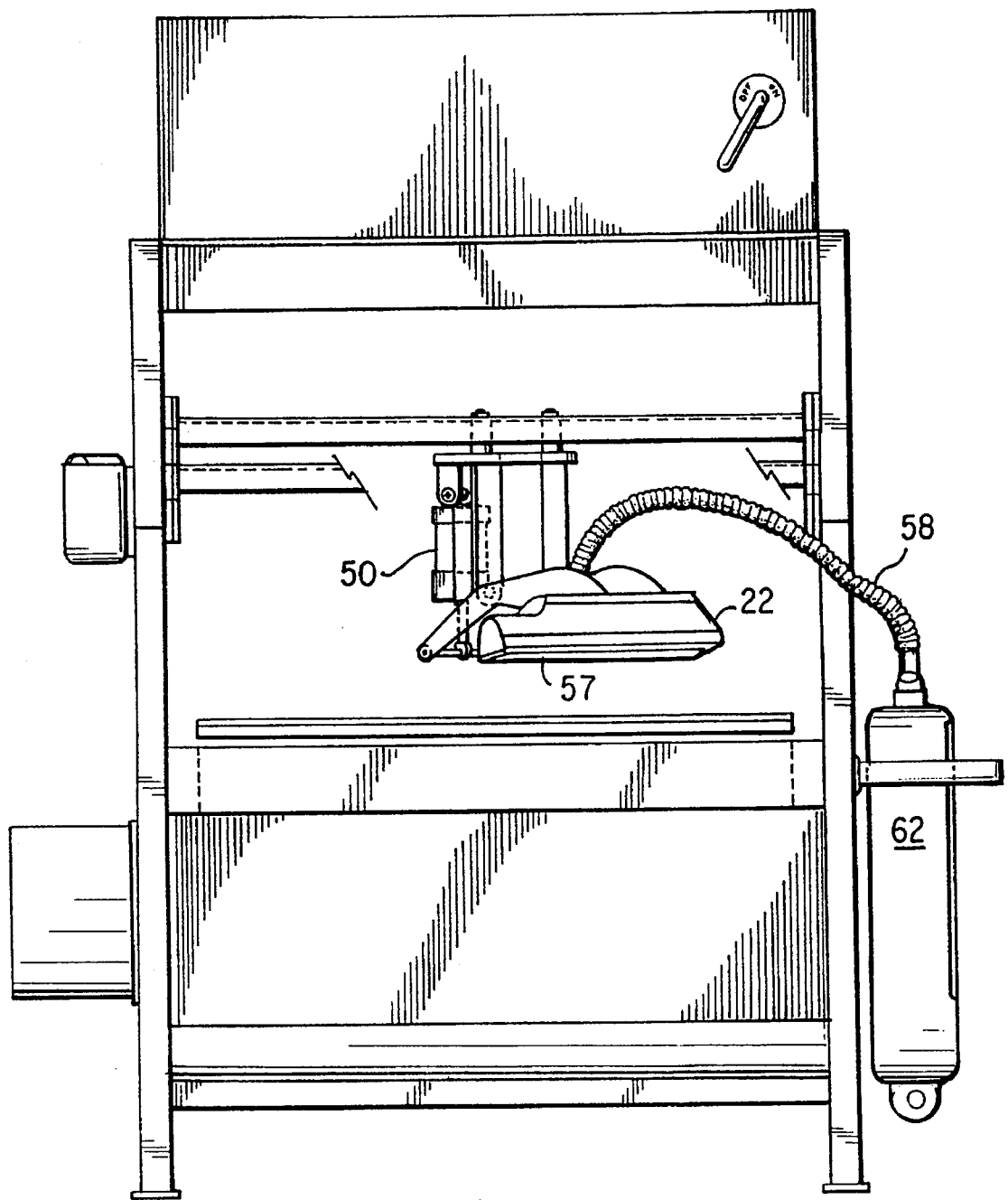
Figure 5:
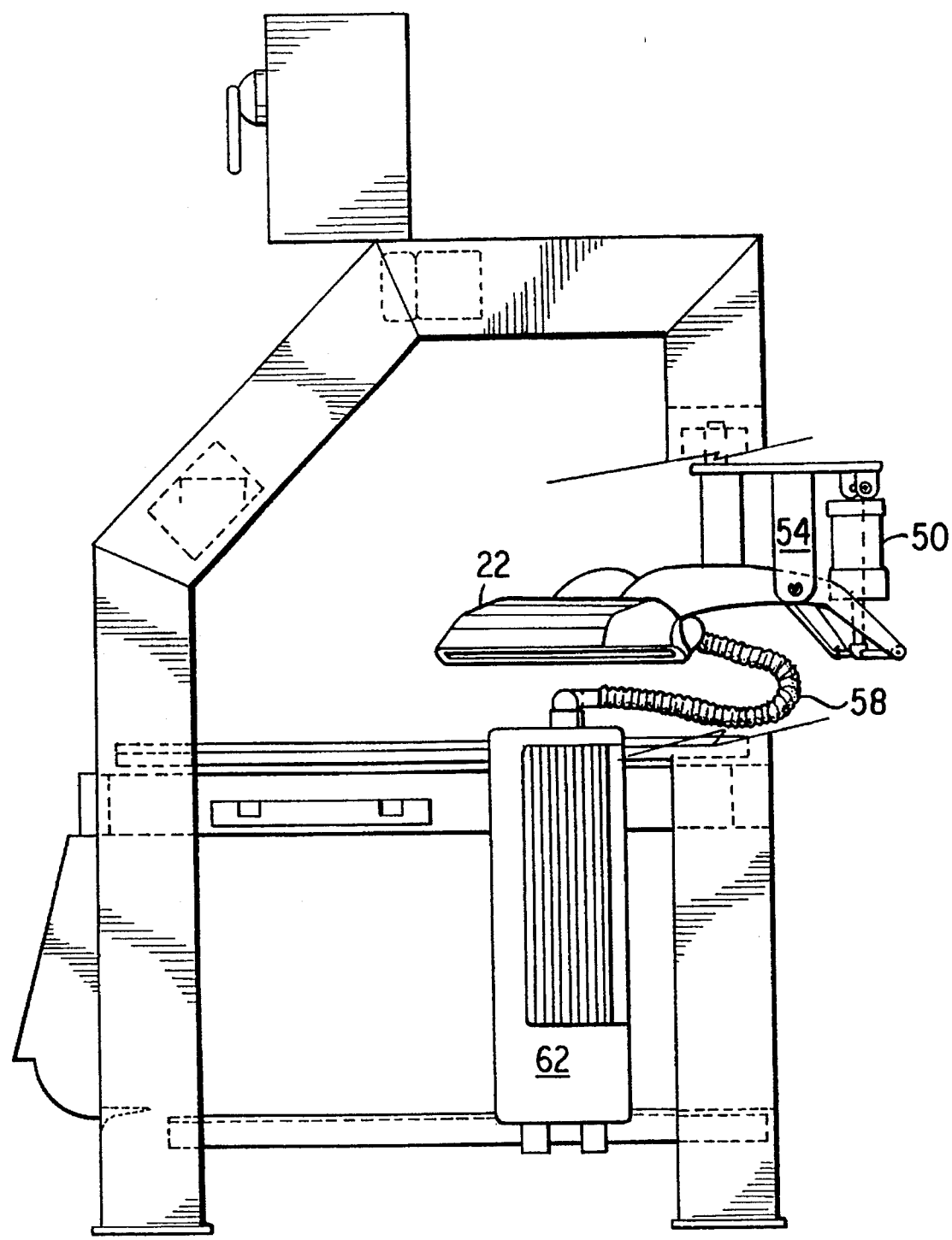
Figure 6:
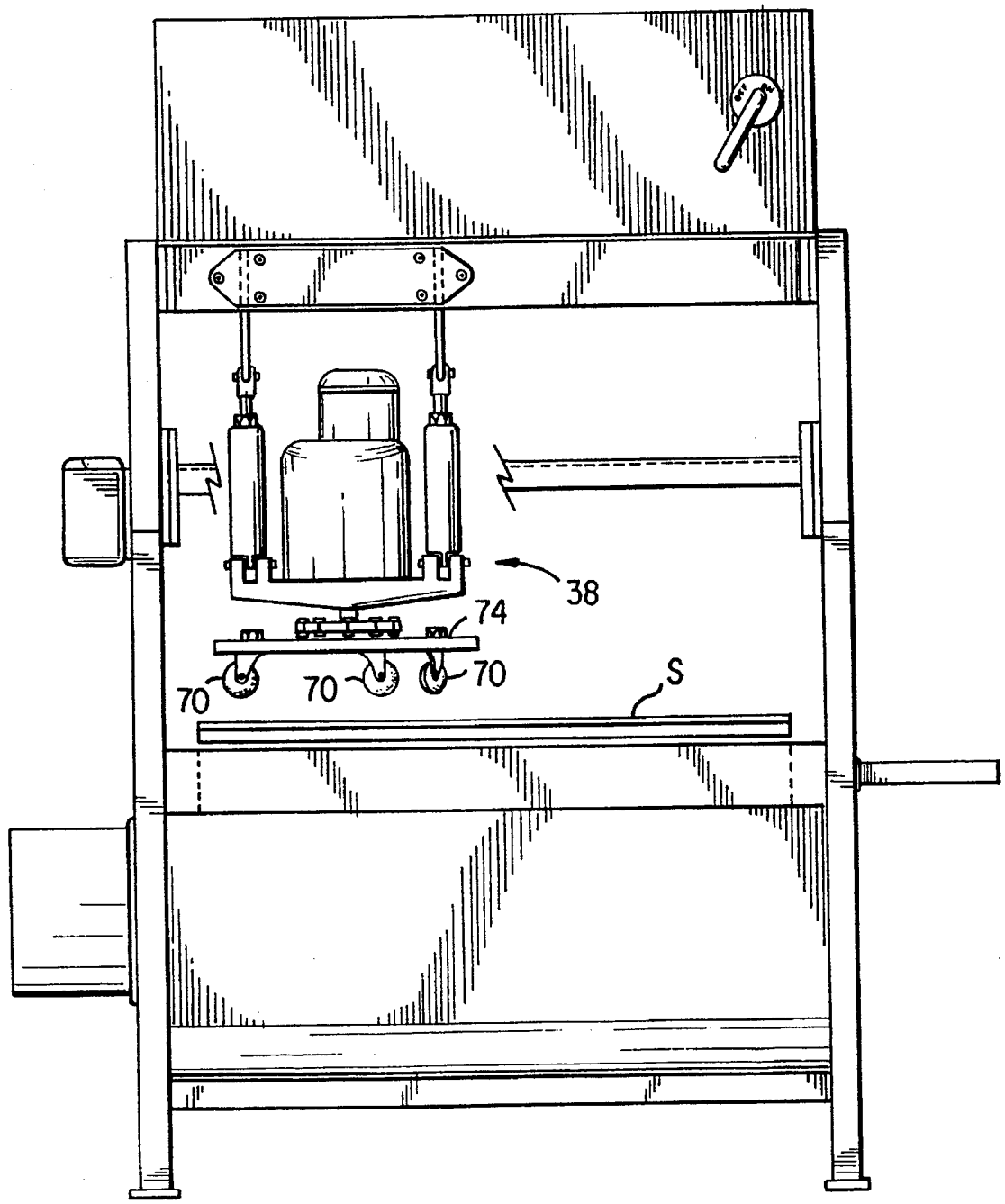
Figure 7:
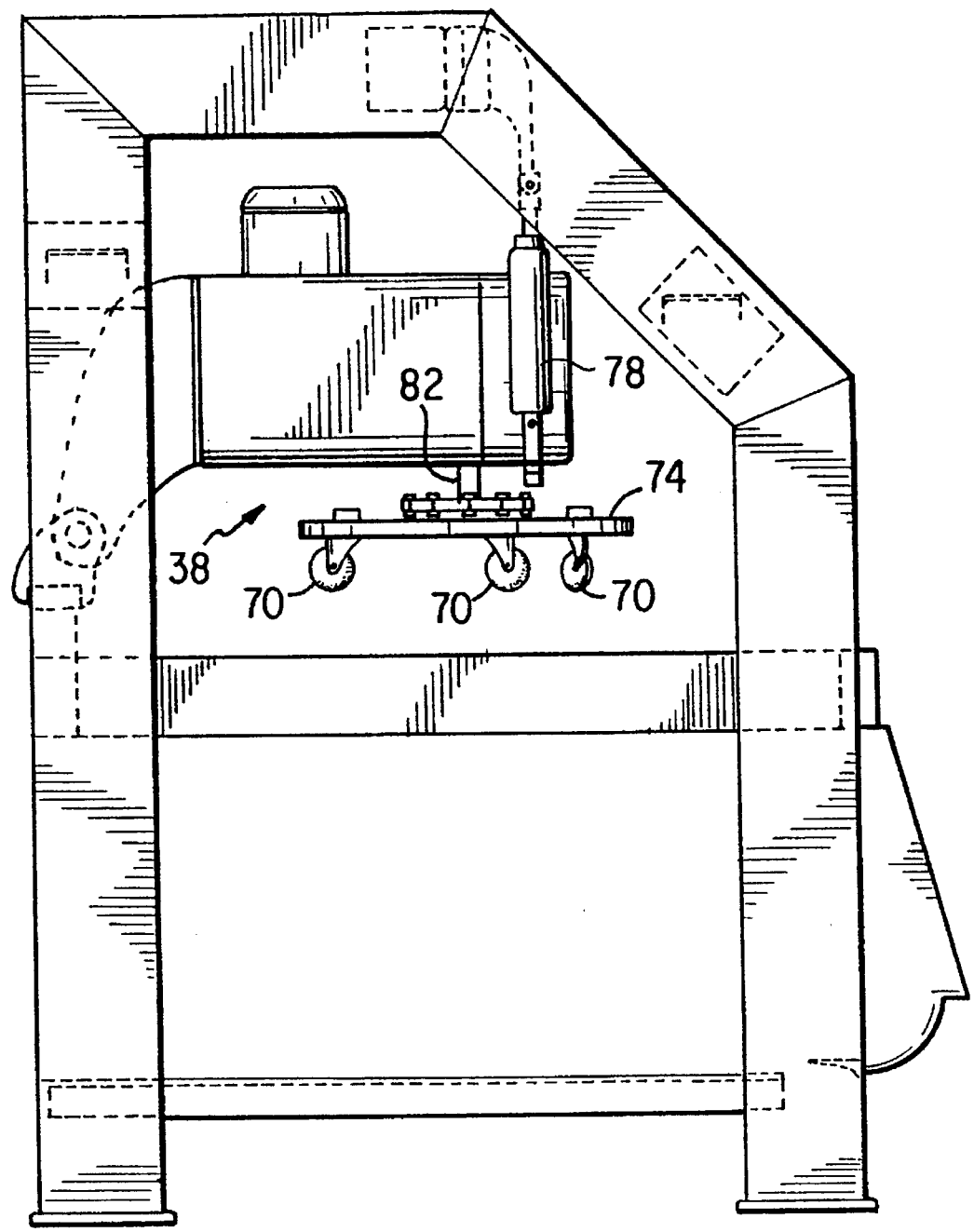
Figure 8:
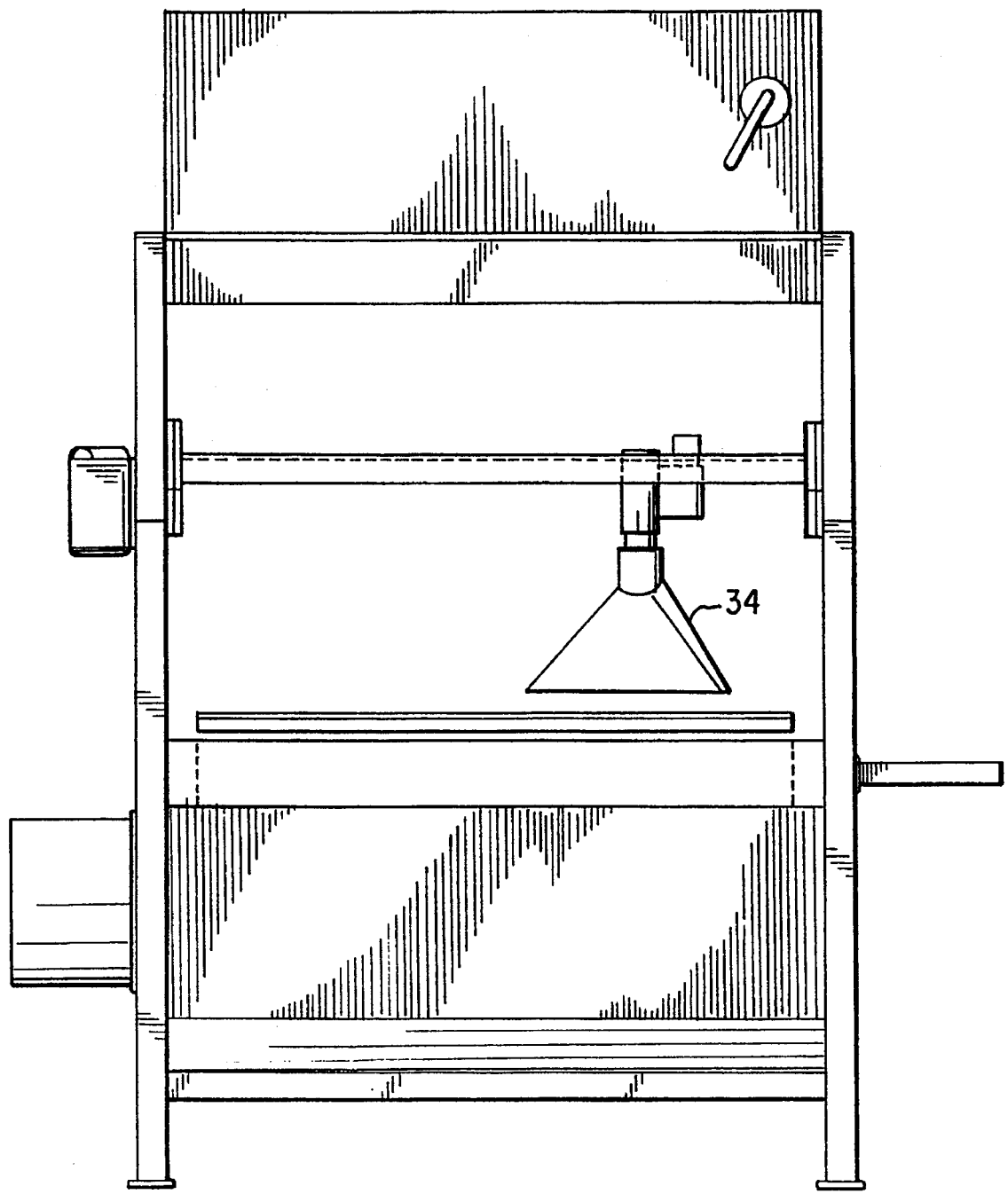
Figure 9:
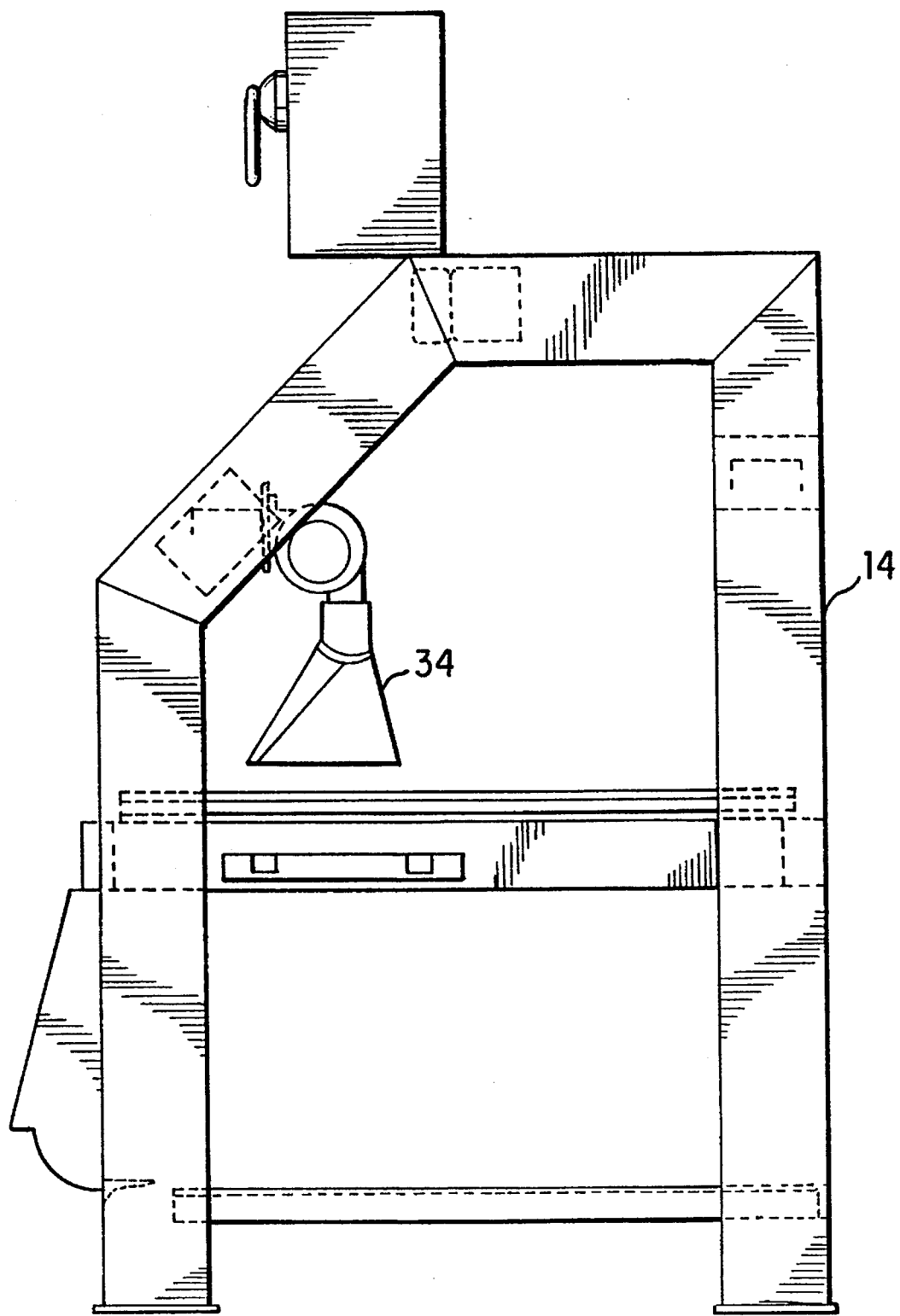
Figure 14B:
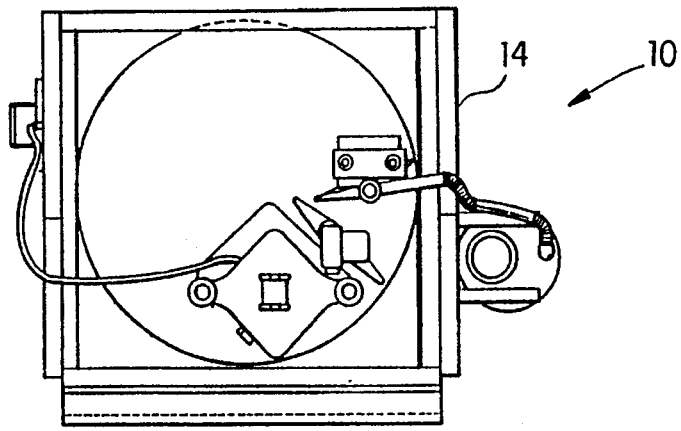
FIGS. 14A–C are views of a portion of the apparatus illustrating, for example, the shampoo head of FIG. 1, the vacuum head of FIGS. 2–3, and the dryer of FIGS. 8–9.
Figure 14A:
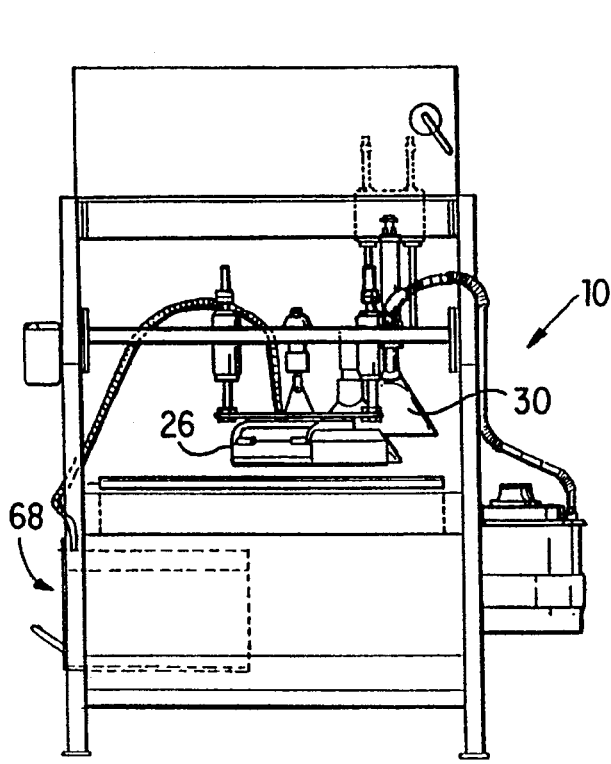
Figure 14C:
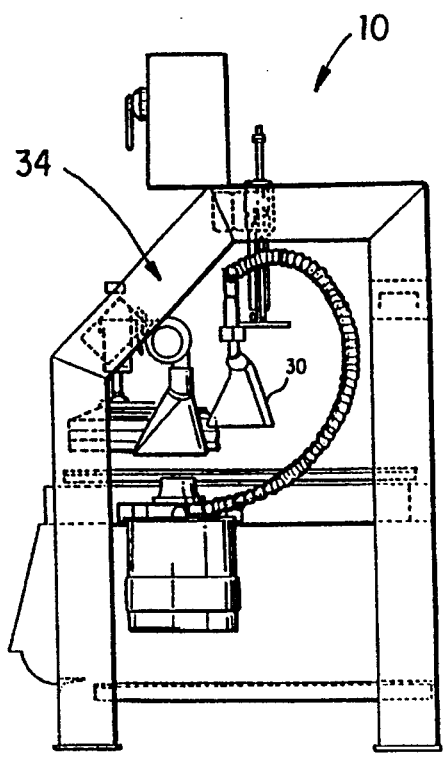
Figure 11:
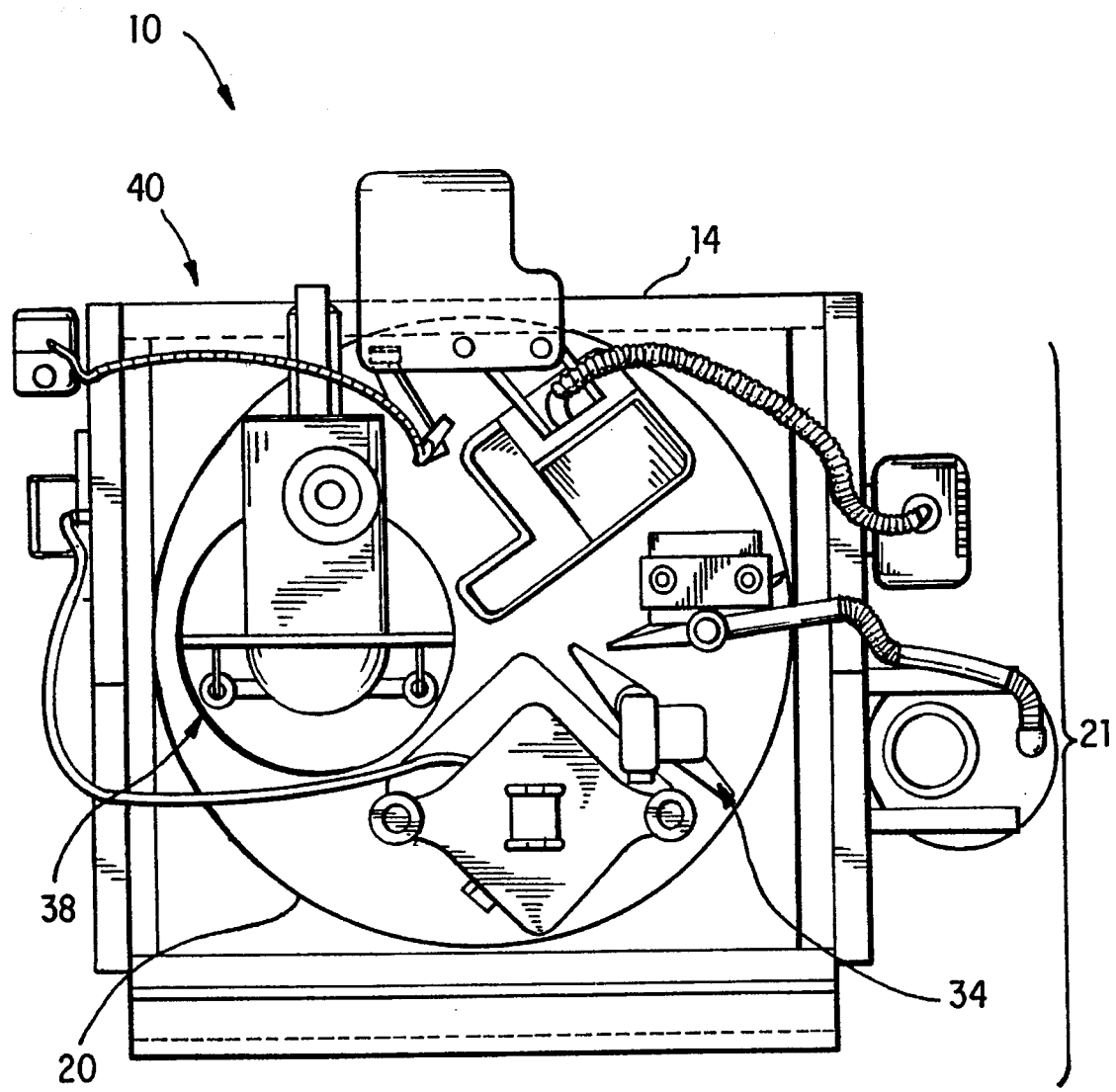
Figure 12B:
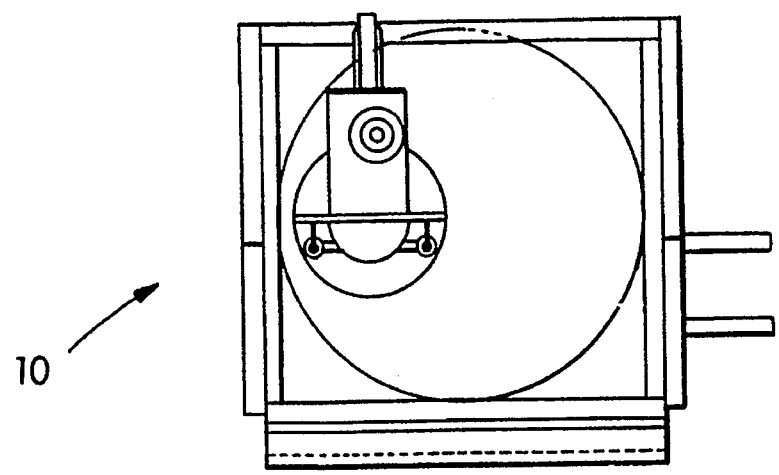
FIGS. 12A–C are views of a portion of the apparatus illustrating, for example, the wear-causing device of FIGS. 6–7.
Figure 12A:
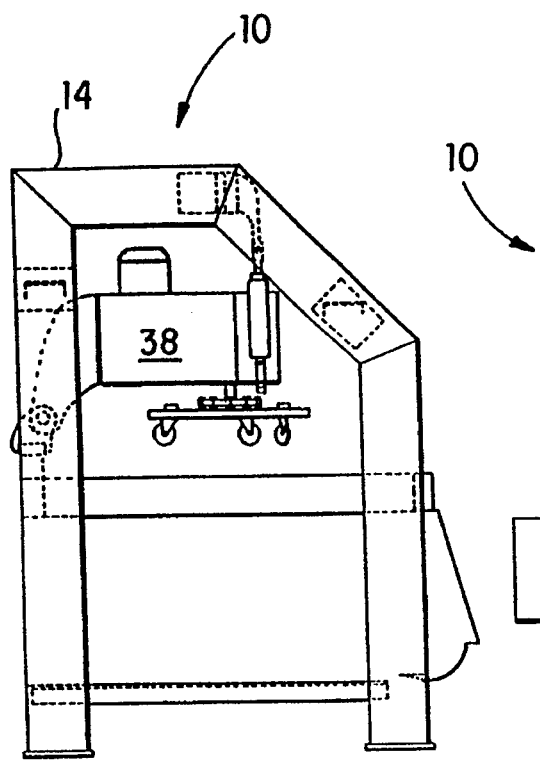
Figure 12C:
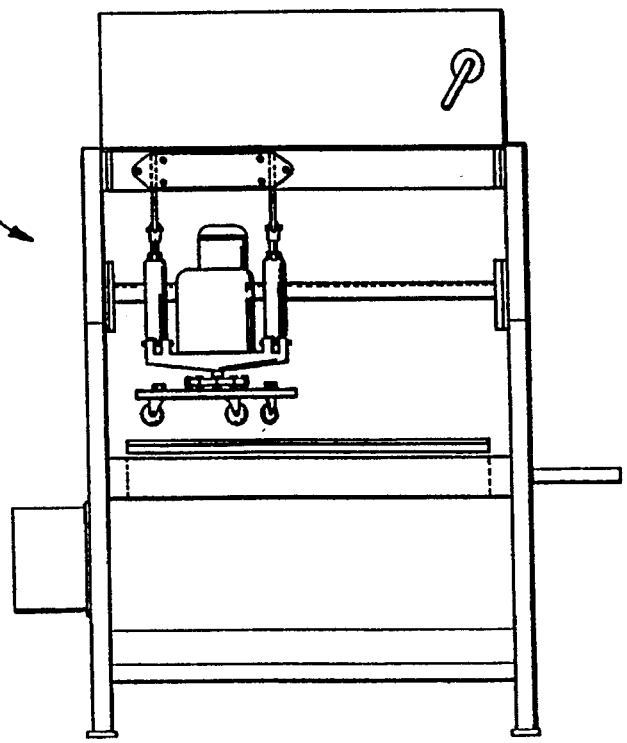
Figure 14B:
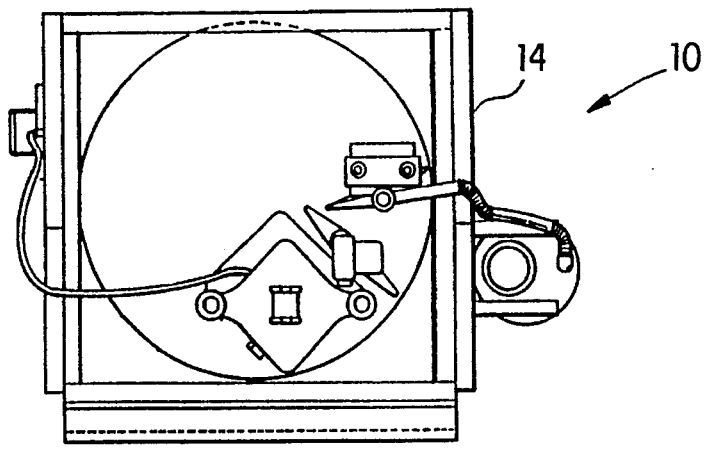
Figure 14A:
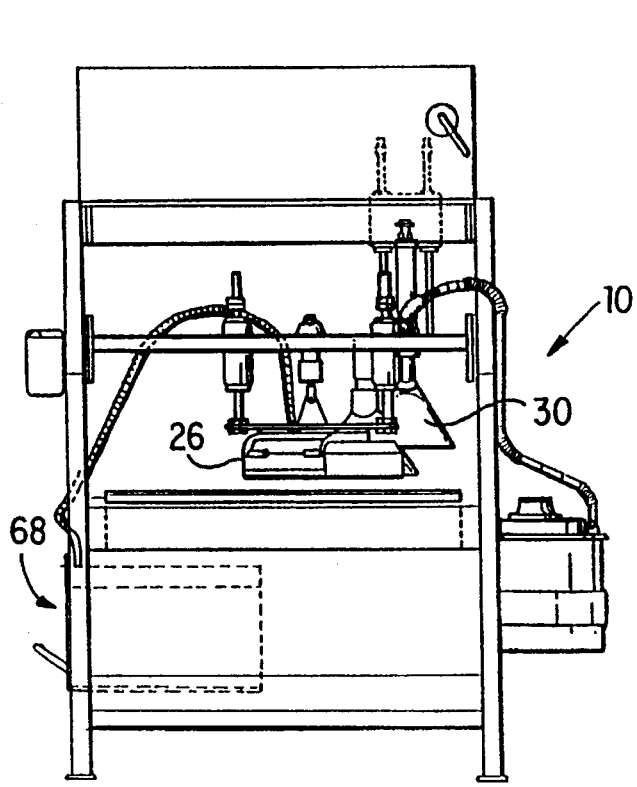
Figure 14C:
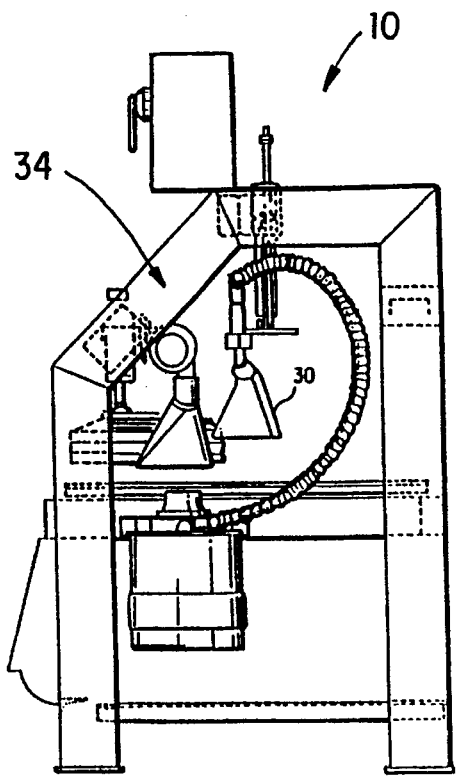

FIGS. 1–14 illustrate an embodiment of an apparatus 10 useful as part of the present invention. Apparatus 10 includes frame 14, programmable controller 18 (such as a microprocessor or other computer), and turntable 20. Also shown in FIGS. 1–14 are various cleaning- or maintenance-related components 21 of apparatus 10, including carpet sweeper 22, shampoo head 26, extraction vacuum head 30, and (hot air) dryer 34, as well as wear-causing device 38. Each of these components 21 is adapted to contact a product P positioned on turntable 20 when desired, to simulate the short- and long-term effects of wear, cleaning, and maintenance on the (upper) surface S of product P. Among the additional components capable of being used with embodiments of apparatus 10 are an automatic soil dispenser, for dispensing soil on product P, and a pre-spray mechanism 40 for loosening embedded soil by saturating portions of the surface S of product P.

Many of components 21 are attached to frame 14 so that they can be raised and lowered relative to the surface S of product P. Pistons 42 and cylinders 46, for example, operate to lower shampoo head 26 onto or adjacent to product P upon command of controller 18, with cylinders 46 being connected to a source of pressurized air. Piston assemblies 50 and 52, also connected to a pressurized air source, similarly permit carpet sweeper 22 and extraction vacuum head 30, respectively, to approach or contact product P, with carpet sweeper 22 adapted to pivot about subframe 54. In the embodiment of apparatus 10 illustrated in FIGS. 1–14, dryer 34 is fixed to frame 14. As with other of components 21, however, dryer 34 too can be modified to move relative to the surface S of product P if necessary or desired.

Carpet sweeper 22, including rotating brush 57, hose 8, and canister 62, may be a standard (dry) vacuum cleaner such as the model LT1600 Lite Trac made by the Castex Company. A Castex Power Eagle 700E1600P may function as shampoo head 26, while extraction vacuum head 30, hose 64, and container 66 may be components of a standard cleaner (such as Castex's Dual Trac DT1200 Wet and Dry Vac) disassembled for mounting on frame 14. Shampoo head 26 communicates with fluid supply 68 (e.g. detergent), while each of components 21 is connected to both a suitable electrical power supply and controller 18.

FIGS. 6–7 and 10–12 illustrate wear-causing device 38, which communicates with controller 18 and includes one or more castors 70 detachably connected to wheel 74. As with components 21, wear-causing device 38 is capable of being raised and lowered relative to the surface S of product P using pressurized air and piston assembly 78. Pressurized air may also be used to force castors 70 against the surface S of product P, with the amount of force varying as a function of the variable pressure of air used. Wheel 74 additionally is connected to shaft 82, permitting it to rotate when castors 70 contact the surface S of product P. Turntable 20, to which product P is affixed for testing, connects to a bidirectional motor and to controller 18.

B. Operation

Figure 15:
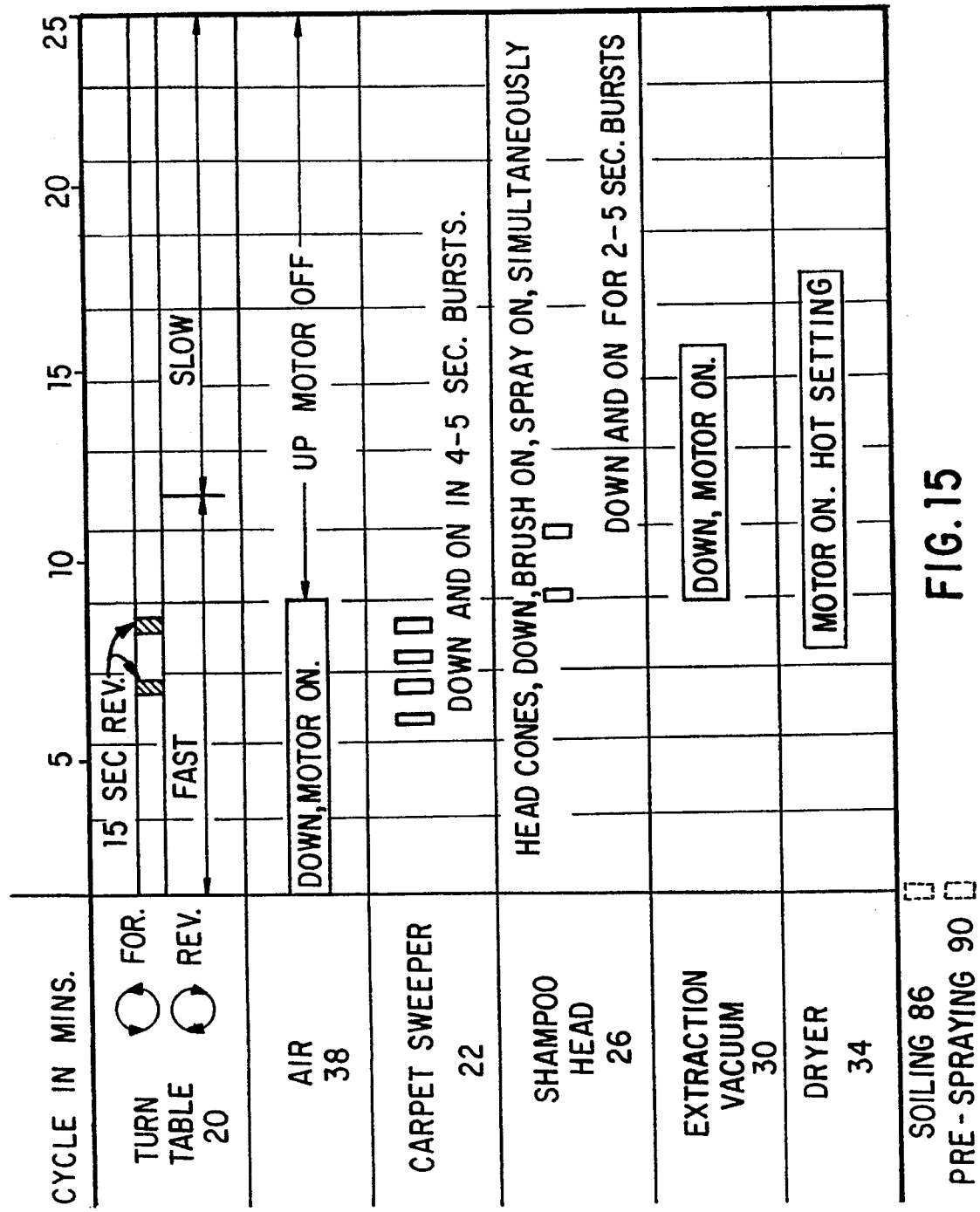
FIG. 15 is an exemplary chart showing the sequencing of operation of components of the apparatus of FIGS. 1–14 as a function of time.

FIG. 15 details a sample testing cycle for product P. As disclosed in FIG. 15, with controller 18 directing turntable 20 to rotate in a selected (nominally "forward") direction at a selected (nominally "fast") speed, wear-causing device 38 is lowered until castors 70 contact and exert a selected amount of pressure against the surface S of product P mounted on turntable 20. Carpet sweeper 22 is then lowered until rotating brush 57 contacts surface S and repeatedly raised and lowered in, e.g., four to five second bursts. Between bursts controller 18 causes turntable 20 to reverse direction repeatedly, simulating the (back and forth) motion typically employed by manual users of conventional carpet sweepers.

Wear-causing device 38 is then raised above surface S and shampoo head 26 lowered periodically to supply cleaning fluid to the product P. Extraction vacuum head 30 additionally is lowered by controller 18 to extract fluid from product P for deposit in container 66, and dryer 34 operated to dry the product P at a lower rotation speed of turntable 20. By examining the color spectra and chemical composition of the fluid contained in container 66, dye fastness and chemical integrity of product P can be evaluated as well.

FIG. 15 shows an approximately twenty-five minute cycle, although differing products P require varying amounts of drying time. Current estimates for carpet tiles, for example, equate a thirty to sixty minute testing cycle with approximately one year of normal use, cleaning, and maintenance. Although FIG. 15 shows optional soiling 86 and pre-spraying 90 of surface S at the start of testing cycle, such materials may be added to the surface S either automatically or manually at any time during the process.

The foregoing is provided for purposes of illustration, explanation, and description of embodiments of the present invention. Modifications and adaptations to these embodiments, including substitution or deletion of various components and changes to cycle times and sequences of operation, for example, will be apparent to those skilled in the art and may be made without departing from the scope or spirit of the invention. Moreover, although the term "carpet" and phrase "carpet tiles" appear in this application to describe the product P under evaluation, the invention may be used with any product capable of being tested in a manner similar to that described.

We claim:

1. A method of contacting a product having a surface, comprising the steps of:
    a. affixing the product to a turntable;
    b. rotating the turntable in a first direction at a first speed;
    c. automatically forcing, using air pressure, a castor against the surface;
    d. automatically contacting the surface with a carpet sweeper;
    e. rotating the turntable in a second direction and automatically contacting the surface with the carpet sweeper while the rotation is in the second direction;
    f. automatically contacting the surface with fluid from a shampoo head;
    g. extracting at least a portion of the fluid from the surface; and
    h. drying the surface.

2. A method according to claim 1 further comprising the step of rotating the turntable at a second speed.

3. A method according to claim 2 further comprising the step of soiling the surface.

4. An apparatus for testing the surface of a product, comprising:
    a. a controller;
    b. a turntable controlled by the controller and to which the product can be affixed;
    c. a wear-causing device controlled by the controller and adapted to contact the surface; and
    d. means, controlled by the controller and having a part adapted to contact the surface while the wear-causing device is not in contact with the surface, for cleaning the product, which cleaning means comprises:
        i. a shampoo head adapted to contact the surface and supply the surface with cleaning fluid;
        ii. an extraction vacuum for extracting at least a portion of the fluid form the surface; and
        iii. a carpet sweeper.

5. An apparatus for testing the surface of a product, comprising:
    a. a controller;
    b. a turntable controlled by the controller and to which the product can be affixed;
    c. a wear-causing device controlled by the controller and adapted to contact the surface, which wear-causing device comprises a castor adapted to contact the surface under force of air pressure; and
    d. means, controlled by the controller, for cleaning the product, which cleaning means comprises:
        i. a shampoo head adapted to contact the surface and supply the surface with cleaning fluid;
        ii. an extraction vacuum for extracting at least a portion of the fluid from the surface; and
        iii. a carpet sweeper.

6. An apparatus according to claim 5 further comprising means, controlled by the controller, for soiling the surface.

7. A method of contacting a product having a surface, comprising the steps of:
    a. contacting the surface with a retractable castor under force of air pressure capable of causing the surface to wear;
    b. dampening the surface with a fluid;
    c. extracting at least a portion of the fluid from the surface while the retractable castor is not contacting the surface; and
    d. automatically moving the surface relative to the castor.

* * * * *

UNITED STATES PATENT AND TRADEMARK OFFICE
CERTIFICATE OF CORRECTION

PATENT NO. : 5,522,251
DATED : June 4, 1996
INVENTOR(S) : Graham A. H. Scott

It is certified that error appears in the above-indentified patent and that said Letters Patent is hereby corrected as shown below:

Column 4, line 15, delete "8" and insert - - 58 - -

Signed and Sealed this

Fifth Day of August, 1997

Attest:

Attesting Officer

BRUCE LEHMAN

Commissioner of Patents and Trademarks